US010279066B2

United States Patent
Chang

(10) Patent No.: US 10,279,066 B2
(45) Date of Patent: May 7, 2019

(54) AROMATIC AGENT CONTAINER

(71) Applicant: Guangzhou Faner Aroma Product Co., Ltd., Guangzhou (CN)

(72) Inventor: Hsu-Hui Chang, Guangzhou (CN)

(73) Assignee: GUANGZHOU FANER AROMA PRODUCT CO., LTD., Guangzhou, Guangdong (CN)

(*) Notice: Subject to any disclaimer, the term of this patent is extended or adjusted under 35 U.S.C. 154(b) by 68 days.

(21) Appl. No.: 15/700,194

(22) Filed: Sep. 11, 2017

(65) Prior Publication Data

US 2019/0076568 A1    Mar. 14, 2019

(51) Int. Cl.
*A61L 9/12* (2006.01)
*H05B 33/08* (2006.01)

(52) U.S. Cl.
CPC .......... *A61L 9/122* (2013.01); *H05B 33/0863* (2013.01); *A61L 2209/10* (2013.01)

(58) Field of Classification Search
CPC ........ A61L 9/122; A61L 9/12; H05B 33/0863
See application file for complete search history.

(56) References Cited

U.S. PATENT DOCUMENTS 5,595,324 A * 1/1997 Brown ............... A47K 5/12
222/1
2003/0020185 A1 * 1/2003 Cox ............... A01M 1/2033
261/26

* cited by examiner

*Primary Examiner* — Sean E Conley
(74) *Attorney, Agent, or Firm* — Leong C. Lei

(57) ABSTRACT

An aromatic agent container includes a container, a supporting bracket and a flow guiding device. The container contains an aromatic agent therein, and its top surface is formed of an opening. The supporting bracket of a ring shape is mounted onto the top of the container. The wall of the supporting bracket is formed of through holes. The flow guiding device is arranged inside the supporting bracket and at a spacing from the top of the container. The flow guiding device includes a driving motor with a fan arranged at an external of the bottom thereof. Accordingly, when the flow guiding device is activated and the fan is driven to rotate for fragrance of the aromatic agent to flow out of the opening of the container, the airflow generated by the fan allows the fragrance to exit from through holes and to spread into the surrounding air effectively and actively.

6 Claims, 4 Drawing Sheets

AROMATIC AGENT CONTAINER

TECHNICAL FIELD OF THE INVENTION

The present invention is related to an aromatic agent container, in particular, to a container capable for spreading the fragrance of an aromatic agent inside the container effectively and actively into the air.

DESCRIPTION OF THE PRIOR ART

With the continuous improvement of living quality, people care about the living in both the physical and mental aspects thereof at greater extend. To eliminate unpleasant odor and dirty air in order to increase the work efficiency and to obtain an optimal mental state, air purifiers are commonly used in indoor spaces for purifying the air; alternatively, aromatic agents are installed to eliminate unpleasant odor indoor spaces.

With regard to the aromatic agents, the use of aromatic agents in an indoor space can provide fragrance to the indoor air continuously for places including, such as, bedrooms, living rooms or toilets such that the living quality can also be improved.

However, the structure of a known aromatic agent mainly uses a container for receiving the liquid-phase or solid-phase aromatic agent (such as, perfume, fragrance oil, essence and fragrance paste etc.) therein, and the container is typically only formed of perforations for the fragrance to emit therefrom such that it only allows the fragrance of the aromatic agent to emit naturally but cannot effectively spread the fragrance to an wide area covering the entire indoor space during the use of such known aromatic agent container.

SUMMARY OF THE INVENTION

In view of the above problem, an objective of the present invention is to provide an aromatic agent container comprising a container, a supporting bracket and a flow guiding device. The container contains an aromatic agent therein and a top surface of the container is formed of an opening formed thereon. The supporting bracket is of a ring shape and is attached onto a top area of the container. In addition, the supporting bracket includes a plurality of through holes formed at a side wall thereof. The flow guiding device comprises a base, a cover, a driving motor, at least one LED light and a press switch. The cover is attached onto a top of the base, and the cover is locked onto the inner wall of the supporting bracket in order to form a spacing between the base of the flow guiding device and the top surface of the container. The internal of the base includes a battery electrically connected to a driving motor, a LED light and a press switch to form a loop. An axle of the driving motor is configured to extend out of a bottom of the base and includes a fan connected thereto such that the fan is arranged at an external of the bottom of the base relatively. The press switch is installed inside the base and arranged corresponding to the press member of the cover.

The technical features of the present invention rely in at least that when the press member of the cover is moved downward due to an external force, the press member touches the press switch to establish an electrical conduction in order to allow the driving motor to drive the fan to rotate. Accordingly, when the fragrance of the aromatic agent flows out from the opening of the container, the airflow generated by the rotations of the fan is able to guide the fragrance of the aromatic agent to flow out from the plurality of through holes of the supporting bracket in order to achieve the effect of spreading the fragrance of the aromatic agent inside the container to the surrounding air effectively and actively. In addition, when the press switch is electrically conducted, the LED light is lit up in order to be used as an indication of the state of use.

DETAILED DESCRIPTION OF THE PREFERRED EMBODIMENTS

Figure 1:
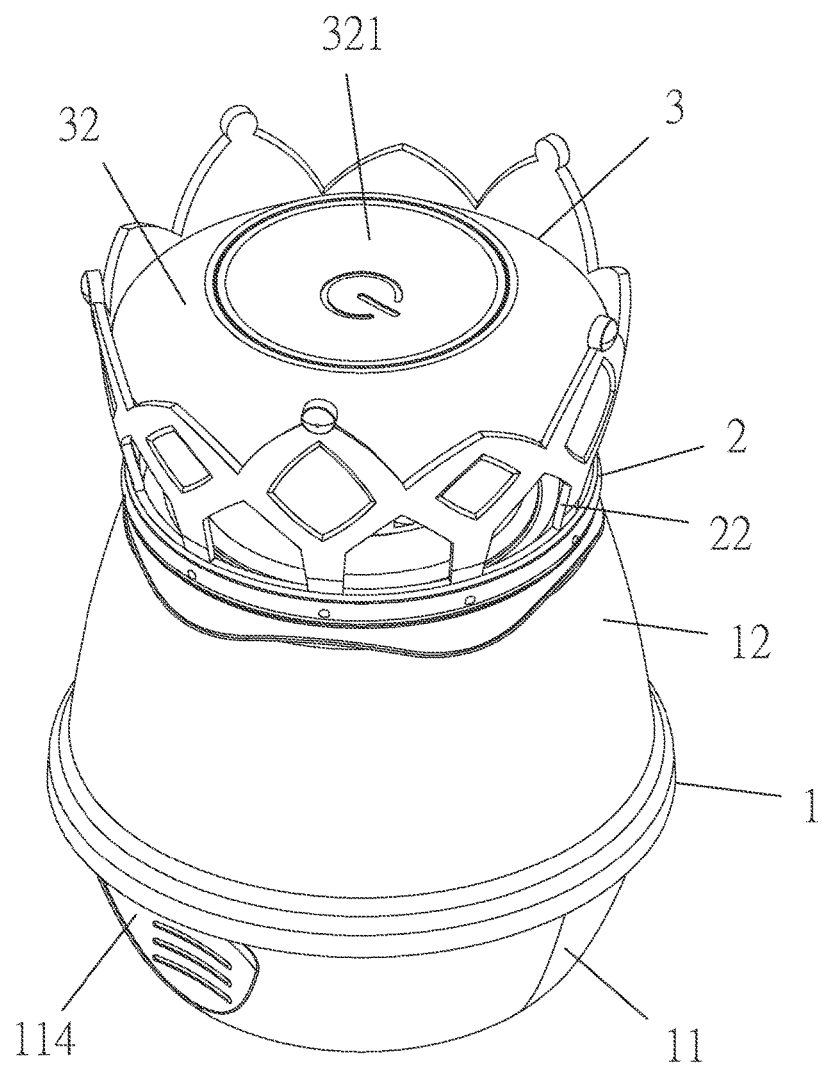
FIG. 1 is a perspective view of the aromatic agent container of the present invention.
Figure 2:
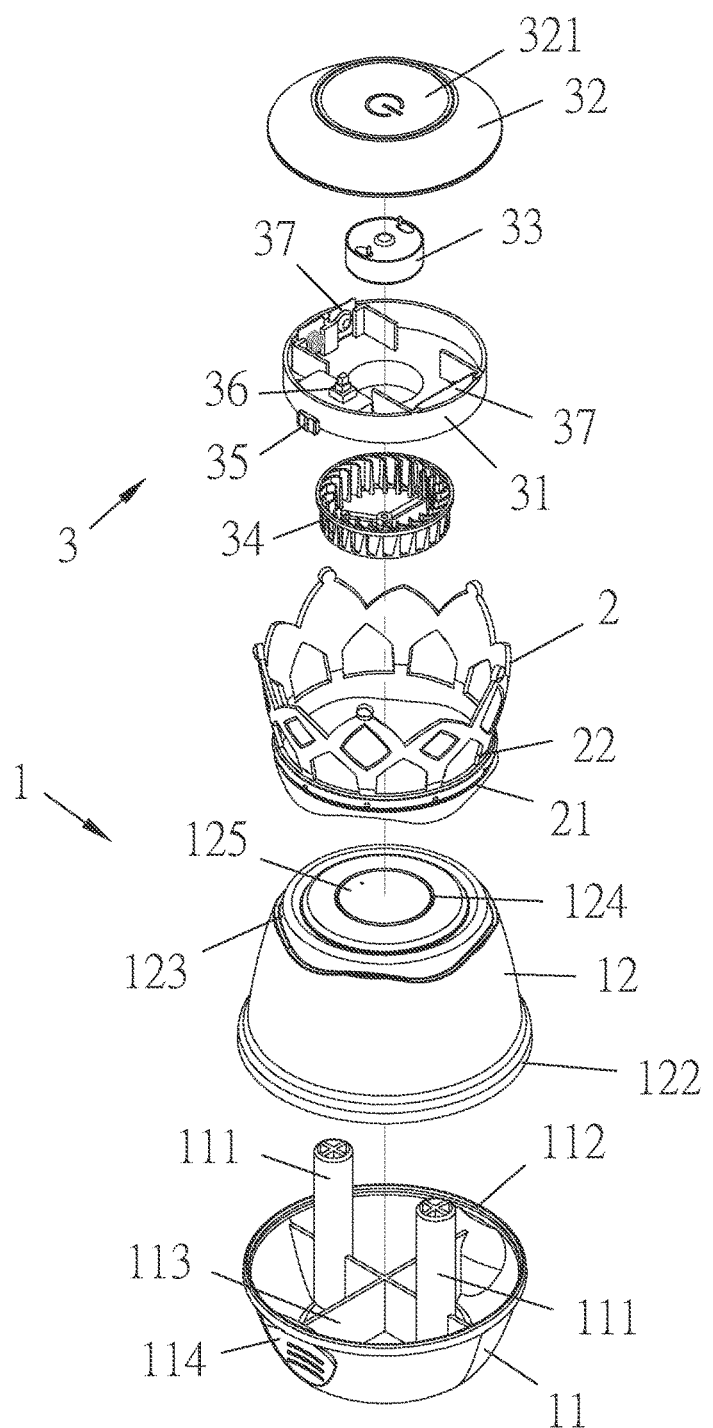
FIG. 2 is an exploded view of the aromatic agent container of the present invention.
Figure 3:
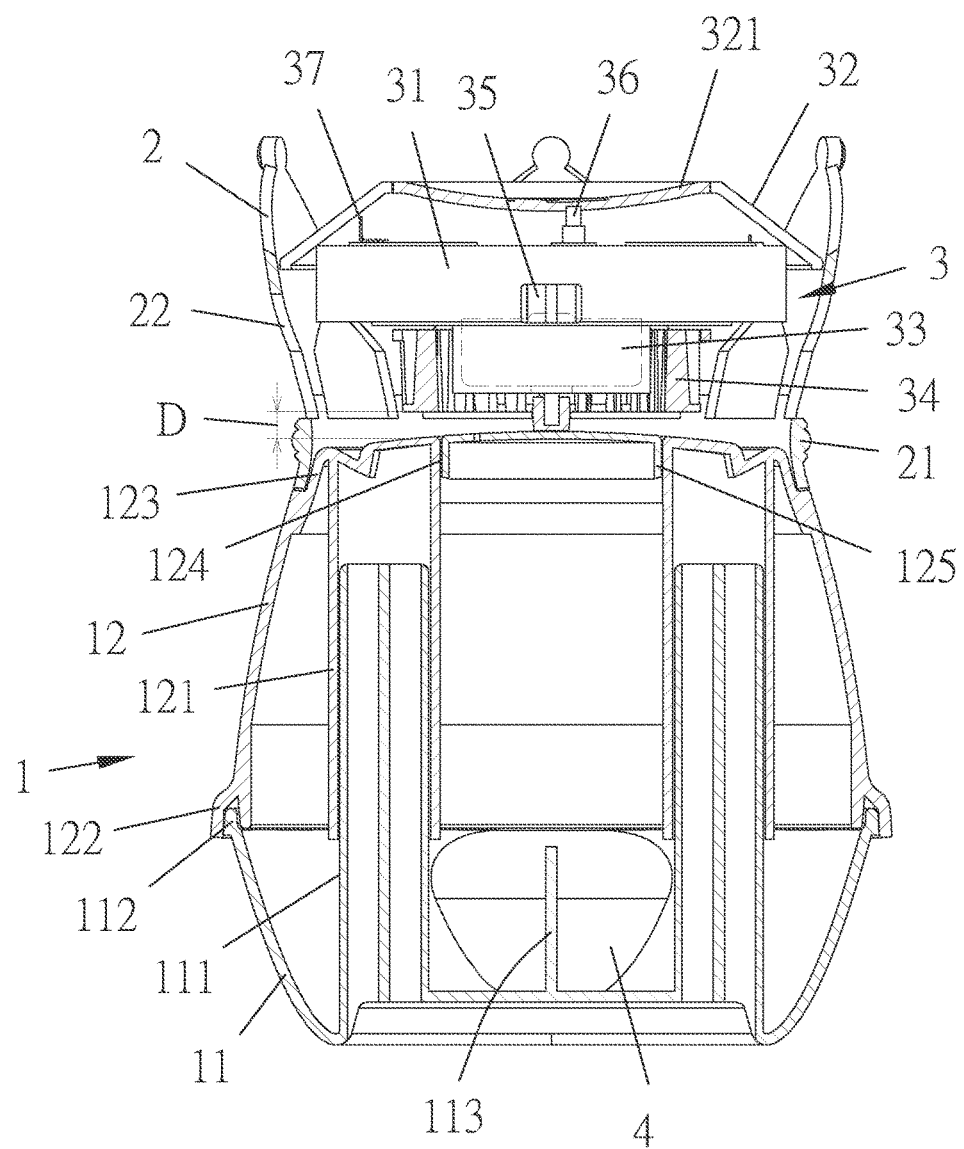
FIG. 3 is a cross sectional side view of the aromatic agent container of the present invention.
Figure 4:
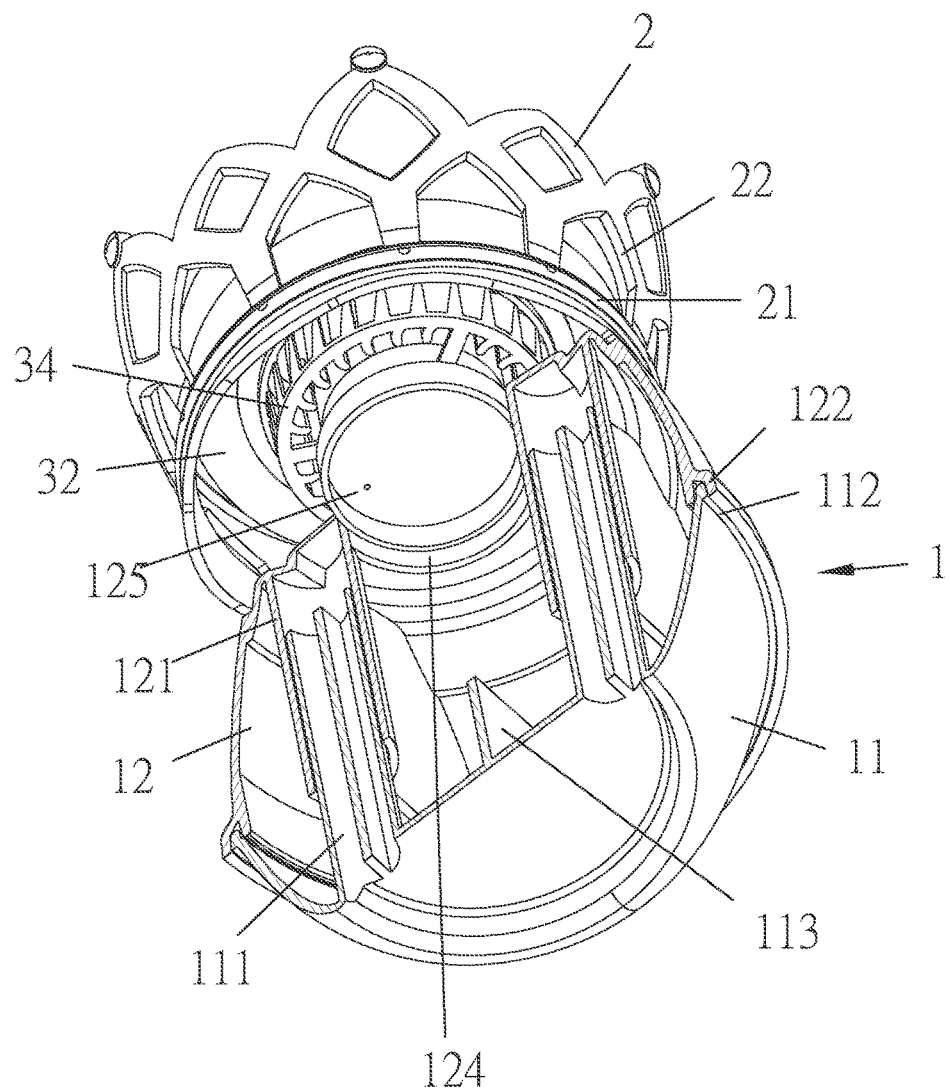
FIG. 4 is a partial cross sectional view of the aromatic agent container of the present invention.

As shown in FIG. 1 to FIG. 4, the present invention provides an aromatic agent container comprising a container 1, a supporting bracket 2 and a flow guiding device 3.

The container 1 is an enclosure for containing at least one aromatic agent 4 therein. For example: the container 1 comprises a first housing 11 and a second housing 12 attached onto each other. The first housing 11 includes at least two first positioning columns 111 formed therein. The first positioning columns 111 can be hollow columns with perforations formed thereon. In addition, the first housing 1 includes a first attachment portion 112 formed at a top edge thereof, and the first housing 11 includes at least one partitioning plate 113 arranged at a bottom of the internal thereof. The aromatic agent 4 is arranged between the partitioning plates 113. Furthermore, at least on holding portion 114 can be formed to indent at an external of the first housing 11. The second housing 12 includes at least two second positioning columns 121 formed therein, and the second positioning columns 121 can be hollow columns. The second positioning columns 121 can be mounted onto the first positioning columns 111, and the bottom edge of the second housing 12 is formed of a second attachment portion 122. The second attachment portion 122 can attach onto the first attachment portion 112. In addition, the second housing 12 includes an opening 124 form at a top surface thereof, and a first mounting portion 123 is formed at a surrounding of the top surface. Furthermore, the second housing 12 includes a cover plate 125 used for covering the opening 124. The container 1 is formed by attaching the first attachment portion 112 onto the second attachment portion 122 of the second housing 12 in order to allow the container 1 to form an enclosure (i.e., the first housing 11 is positioned at the bottom area of the container, and the second housing 12 is positioned at the top area of the container 1). Moreover, when the first housing 11 and the second housing 12 are attached onto each other, the second positioning columns 121 of the second housing 12 can be mounted onto the first positioning columns 111 of the first housing 11. With the utilization of the first positioning columns 111 being hollow columns with perforations, the second positioning columns 121 can be mounted onto the first positioning columns 111 of the first housing 11 with ease.

The supporting bracket 2 is of a ring shape and is attached onto the top area of the container 1. The supporting bracket 2 includes a second mounting portion 21 at a bottom thereon. The second mounting portion 21 is mounted onto the first mounting portion 123 of the second housing 12 of the container 1 in order to allow the supporting bracket 2 to be secured onto the container at the top area thereof. Furthermore, the supporting bracket includes a plurality of through holes 22 formed at a side wall thereof. The supporting bracket 2 can be of any arbitrary shapes; for example, the supporting bracket 2 can be of a crown shape.

The flow guiding device 3 is installed inside the supporting bracket 2 and is arranged at a spacing D away from the top surface of the container 1. The flow guiding device 3 comprises a base 31, a cover 32, a driving motor 33, at least one LED light 35 and a press switch 36. The internal of the base 31 includes at least two power connection ports 37 formed therein, and the base 31 can be installed with a battery such that the two power connection ports 37 are electrically connected to the positive and negative electrodes of the battery. The cover 32 is attached onto the base 31, and the diameter of the cover 32 is greater than the diameter of the base 31. The cover 32 is locked onto the inner wall of the supporting bracket 2 in order to form a spacing D between the base 31 of the flow guiding device 3 and the top surface of the container 1. Furthermore, the cover 32 includes a press member 321 disposed thereon. The driving motor 33 is installed inside the base 31, and the axle of the driving motor 33 extends out of the bottom of the base 31 and is connected with a fan 34. The fan 34 is arranged at an external of the bottom of the base 31 relatively. The driving motor 33, the LED light 35, the press switch 36 and the two power connection ports 37 are electrically connected to each other to form a loop.

According to an embodiment of the aromatic agent container of the present invention, during the use thereof, the cover plate 125 arranged on the second housing 12 can be removed in order to allow the fragrance of the aromatic agent inside the container 1 to flow out of the opening 124 of the second housing 12. When the press member 321 of the cover 32 is moved downward due to an external force, the press member 32 touches the press switch 36 to establish an electrical conduction in order to allow the driving motor 33 to drive the fan 34 to rotate. With the airflow generated by the rotations of the fan 34, the fragrance of the aromatic agent 4 is able to flow out of the plurality of through holes 22 of the supporting bracket 22 in order to achieve the effect of spreading the fragrance of the aromatic agent 4 inside the container 1 into the surrounding air.

When the press switch 36 is electrically conducted, the LED light 35 is lit up, which can be used as an indication of the state of use thereof.

I claim:

1. An aromatic agent container comprising:
    a container having an enclosure member for containing at least one aromatic agent therein; the container having a first mounting portion formed at a surrounding of a top surface thereof, and the top surface of the container having an opening formed thereon;
    a supporting bracket having a ring shape and attached onto a top area of the container; the supporting bracket having a second mounting portion formed at a bottom thereof; the second mounting portion configured to attach onto the first mounting portion in order to allow the supporting bracket to secure at the top area of the container; the supporting bracket having a plurality of through holes formed at a side wall thereof;
    a flow guiding device installed inside the bracket and arranged at a space away from the top surface of the container; the flow guiding device comprising a base, a cover, a driving motor, at least one LED light and a press switch; the base having at least two power connection ports formed therein; the two power connection ports configured to connect with positive and negative electrodes of a battery; the cover attached onto a top of the base and having a diameter greater than a diameter of the base; the cover configured to lock onto an inner wall of the supporting bracket, the cover having a press member arranged thereon; the driving motor installed inside the base, and an axle of the driving motor configured to extend out of a bottom of the base and having a fan connected thereto; the fan arranged at an external of the bottom of the base relatively; the LED light installed on an external side wall of the base; the press switch installed inside the base and arranged corresponding to the press member of the cover; and
    wherein the driving motor, the LED light, the press switch and the two power connection ports are electrically connected to each other to form a loop, thereby when the press member of the cover is moved downward due to an external force, the press member touches the press switch to establish an electrical conduction in order to allow the driving motor to drive the fan to rotate and to lit up the LED light.

2. The aromatic agent container according to claim 1, wherein the container comprises a first housing and a second housing attached onto each other; the first housing includes at least two first positioning columns formed therein and a first attachment portion formed at a top edge thereof; the second housing includes at least two second positioning columns formed therein for mounting onto the first positioning columns and a second attachment portion formed at a bottom edge thereof; wherein the container is formed by attaching the first attachment portion of the first housing onto the second attachment portion of the second housing in order to allow the first housing to be positioned at a top portion of the container, the second housing to be positioned at a bottom portion of the container, the opening to be positioned at a top surface of the second housing and the first attachment portion to be positioned at a surrounding of the top surface of the second housing.

3. The aromatic agent container according to claim 2, wherein the first positioning columns can be hollow columns with perforations formed thereon, and the second positioning columns can be hollow columns.

4. The aromatic agent container according to claim 2, wherein the first housing includes at least one partitioning plate installed therein and arranged at a bottom surface.

5. The aromatic agent container according to claim 2, wherein the first housing includes at least one holding portion formed to indent at an external thereof.

6. The aromatic agent container according to claim 2, wherein the second housing further includes a cover plate for covering the opening.

\* \* \* \* \*